United States Patent
Bouwstra et al.

(10) Patent No.: US 8,080,515 B2
(45) Date of Patent: *Dec. 20, 2011

(54) METHOD FOR PREVENTION OF PLATELET AGGREGATION EMPLOYING AND RGD-ENRICHED GELATINE-LIKE PROTEIN

(75) Inventors: Jan Bastiaan Bouwstra, Bilthoven (NL); Andries Johannes Jozef Van Es, Dorst (NL); Yuzo Toda, Goirle (NL)

(73) Assignee: Fuji Film Manufacturing Europe B.V., Tilburg (NL)

( * ) Notice: Subject to any disclaimer, the term of this patent is extended or adjusted under 35 U.S.C. 154(b) by 204 days.

This patent is subject to a terminal disclaimer.

(21) Appl. No.: 12/494,450

(22) Filed: Jun. 30, 2009

(65) Prior Publication Data

US 2010/0048477 A1     Feb. 25, 2010

Related U.S. Application Data

(60) Continuation of application No. 11/770,256, filed on Jun. 28, 2007, now Pat. No. 7,560,427, which is a division of application No. 10/550,786, filed as application No. PCT/NL2004/000208 on Mar. 26, 2004, now Pat. No. 7,517,954.

(30) Foreign Application Priority Data

Mar. 28, 2003    (EP) .................................... 03075906

(51) Int. Cl.
     *C07K 14/00*    (2006.01)
(52) U.S. Cl. .......................................... 514/1; 530/350
(58) Field of Classification Search ....... 514/1; 530/350
     See application file for complete search history.

(56) References Cited

U.S. PATENT DOCUMENTS

| | | | |
|---|---|---|---|
| 5,721,213 A * | 2/1998 | Sato et al. ..................... | 514/13.7 |
| 6,140,072 A | 10/2000 | Ferrari et al. | |
| 6,146,824 A | 11/2000 | Bar-Shavit | |
| 6,992,172 B1 | 1/2006 | Chang et al. | |
| 7,517,954 B2 | 4/2009 | Bouwstra et al. | |
| 7,560,427 B2 | 7/2009 | Bouwstra et al. | |
| 7,598,347 B2 | 10/2009 | Bouwstra et al. | |
| 7,645,737 B2 | 1/2010 | Bouwstra et al. | |
| 7,671,016 B2 | 3/2010 | Bouwstra et al. | |

FOREIGN PATENT DOCUMENTS

| | | |
|---|---|---|
| WO | WO 98/18918 | 5/1998 |
| WO | WO 02/064625 | 8/2002 |

OTHER PUBLICATIONS

International Search Report of PCT/NL2004/00208 dated Feb. 16, 2005.

Wierzba et al., "Production and Properties fo a Bifunctional Fusion . . . ", Biotechnology and Bioengineering . . . , Jul. 20, 1995, vol. 47, pp. 147-154, John Wiley & Sons, New York,US.

Zhao et al., Synthesis of RGD containing peptides and their bioactivities. Preparative Biochemistry & Biotechnology 32(4): 2002, 363-3890.

Oku et al., "Liposomal Arg-Gly-Asp analogs effectively inhibit metastatic B16 melanoma colonization in murine lungs.", Life Sciences, 1996, 58(24): 2263-2270.

\* cited by examiner

*Primary Examiner* — Karen Carlson
(74) *Attorney, Agent, or Firm* — K&L Gates LLP

(57) ABSTRACT

The invention concerns a cell support comprising an RGD-enriched gelatine that has a more even distribution of RGD sequences than occurring in a natural gelatine and with a minimum level of RGD sequences. More precise the percentage of RGD sequences related to the total number of amino acids is at least 0.4 and if the RGD-enriched gelatine comprises 350 amino acids or more, each stretch of 350 amino acids contains at least one RGD motif. Preferably the RGD-enriched gelatines are prepared by recombinant technology, and have a sequence that is derived from a human gelatine or collagen amino acid sequence. The invention also relates to RGD-enriched gelatines that are used for attachment to integrins. In particular The RGD-enriched gelatines of the invention are suitable for coating a cell culture support for growing anchor-dependant cell types. Further, the RGD-enriched gelatines of the invention may find use in medical applications, in particular as a coating on implant or transplant material or as a component of drug delivery systems.

9 Claims, No Drawings

SEQUENCE LISTING

```
<160> NUMBER OF SEQ ID NOS: 3

<210> SEQ ID NO 1
<211> LENGTH: 250
<212> TYPE: PRT
<213> ORGANISM: Artificial sequence
<220> FEATURE:
<223> OTHER INFORMATION: Human partial COL1A1-sequence

<400> SEQUENCE: 1

Pro Pro Gly Pro Ala Gly Pro Ala Gly Glu Arg Gly Glu Gln Gly Pro
1               5                   10                  15

Ala Gly Ser Pro Gly Phe Gln Gly Leu Pro Gly Pro Ala Gly Pro Pro
            20                  25                  30

Gly Glu Ala Gly Lys Pro Gly Glu Gln Gly Val Pro Gly Asp Leu Gly
        35                  40                  45

Ala Pro Gly Pro Ser Gly Ala Arg Gly Glu Arg Gly Phe Pro Gly Glu
    50                  55                  60

Arg Gly Val Gln Gly Pro Pro Gly Pro Ala Gly Pro Arg Gly Ala Asn
65                  70                  75                  80

Gly Ala Pro Gly Asn Asp Gly Ala Lys Gly Asp Ala Gly Ala Pro Gly
                85                  90                  95

Ala Pro Gly Ser Gln Gly Ala Pro Gly Leu Gln Gly Met Pro Gly Glu
            100                 105                 110

Arg Gly Ala Ala Gly Leu Pro Gly Pro Lys Gly Asp Arg Gly Asp Ala
        115                 120                 125

Gly Pro Lys Gly Ala Asp Gly Ser Pro Gly Lys Asp Gly Val Arg Gly
    130                 135                 140

Leu Thr Gly Pro Ile Gly Pro Pro Gly Pro Ala Gly Ala Pro Gly Asp
145                 150                 155                 160

Lys Gly Glu Ser Gly Pro Ser Gly Pro Ala Gly Pro Thr Gly Ala Arg
```

```
                     165                 170                 175
Gly Ala Pro Gly Asp Arg Gly Glu Pro Gly Pro Pro Gly Pro Ala Gly
                180                 185                 190

Phe Ala Gly Pro Pro Gly Ala Asp Gly Gln Pro Gly Ala Lys Gly Glu
            195                 200                 205

Pro Gly Asp Ala Gly Ala Lys Gly Asp Ala Gly Pro Pro Gly Pro Ala
        210                 215                 220

Gly Pro Ala Gly Pro Pro Gly Pro Ile Gly Asn Val Gly Ala Pro Gly
225                 230                 235                 240

Ala Lys Gly Ala Arg Gly Ser Ala Gly Pro
                245                 250

<210> SEQ ID NO 2
<211> LENGTH: 252
<212> TYPE: PRT
<213> ORGANISM: Artificial sequence
<220> FEATURE:
<223> OTHER INFORMATION: Repeated partial human COL1A1-1 sequence

<400> SEQUENCE: 2

Gly Ala Pro Gly Ser Gln Gly Ala Pro Gly Leu Gln Gly Met Pro Gly
1               5                   10                  15

Glu Arg Gly Ala Ala Gly Leu Pro Gly Pro Lys Gly Asp Arg Gly Asp
                20                  25                  30

Ala Gly Pro Lys Gly Ala Asp Gly Ser Pro Gly Lys Asp Gly Val Arg
            35                  40                  45

Gly Leu Thr Gly Pro Ile Gly Pro Pro Gly Pro Ala Gly Ala Pro Gly
        50                  55                  60

Ala Pro Gly Ser Gln Gly Ala Pro Gly Leu Gln Gly Met Pro Gly Glu
65                  70                  75                  80

Arg Gly Ala Ala Gly Leu Pro Gly Pro Lys Gly Asp Arg Gly Asp Ala
                85                  90                  95

Gly Pro Lys Gly Ala Asp Gly Ser Pro Gly Lys Asp Gly Val Arg Gly
            100                 105                 110

Leu Thr Gly Pro Ile Gly Pro Pro Gly Pro Ala Gly Ala Pro Gly Ala
        115                 120                 125

Pro Gly Ser Gln Gly Ala Pro Gly Leu Gln Gly Met Pro Gly Glu Arg
    130                 135                 140

Gly Ala Ala Gly Leu Pro Gly Pro Lys Gly Asp Arg Gly Asp Ala Gly
145                 150                 155                 160

Pro Lys Gly Ala Asp Gly Ser Pro Gly Lys Asp Gly Val Arg Gly Leu
                165                 170                 175

Thr Gly Pro Ile Gly Pro Pro Gly Pro Ala Gly Ala Pro Gly Ala Pro
            180                 185                 190

Gly Ser Gln Gly Ala Pro Gly Leu Gln Gly Met Pro Gly Glu Arg Gly
        195                 200                 205

Ala Ala Gly Leu Pro Gly Pro Lys Gly Asp Arg Gly Asp Ala Gly Pro
    210                 215                 220

Lys Gly Ala Asp Gly Ser Pro Gly Lys Asp Gly Val Arg Gly Leu Thr
225                 230                 235                 240

Gly Pro Ile Gly Pro Pro Gly Pro Ala Gly Ala Pro
                245                 250

<210> SEQ ID NO 3
<211> LENGTH: 625
<212> TYPE: PRT
<213> ORGANISM: Artificial sequence
```

<220> FEATURE:
<223> OTHER INFORMATION: Human Partial COL5A2 sequence

<400> SEQUENCE: 3

```
Gln Gly Pro Ile Gly Pro Pro Gly Glu Glu Gly Lys Arg Gly Pro Arg
1               5                   10                  15

Gly Asp Pro Gly Thr Leu Gly Pro Pro Gly Val Gly Glu Arg Gly
            20                  25                  30

Ala Pro Gly Asn Arg Gly Phe Pro Gly Ser Asp Gly Leu Pro Gly Pro
            35                  40                  45

Lys Gly Ala Gln Gly Glu Arg Gly Pro Val Gly Ser Ser Gly Pro Lys
50                  55                  60

Gly Ser Gln Gly Asp Pro Gly Arg Pro Gly Glu Pro Gly Leu Pro Gly
65                  70                  75                  80

Ala Arg Gly Leu Thr Gly Asn Pro Gly Val Gln Gly Pro Glu Gly Lys
                85                  90                  95

Leu Gly Pro Leu Gly Ala Pro Gly Glu Asp Gly Arg Pro Gly Pro Pro
                100                 105                 110

Gly Ser Ile Gly Ile Lys Gly Gln Pro Gly Thr Met Gly Leu Pro Gly
            115                 120                 125

Pro Lys Gly Ser Asn Gly Asp Pro Gly Lys Pro Gly Glu Ala Gly Asn
130                 135                 140

Pro Gly Val Pro Gly Gln Arg Gly Ala Pro Gly Lys Asp Gly Lys Val
145                 150                 155                 160

Gly Pro Tyr Gly Pro Pro Gly Pro Pro Gly Leu Arg Gly Glu Arg Gly
                165                 170                 175

Glu Gln Gly Pro Pro Gly Pro Thr Gly Phe Gln Gly His Pro Gly Pro
                180                 185                 190

Pro Gly Pro Pro Gly Glu Gly Gly Lys Pro Gly Asp Gln Gly Val Pro
            195                 200                 205

Gly Gly Pro Gly Ala Val Gly Pro Leu Gly Pro Arg Gly Glu Arg Gly
            210                 215                 220

Asn Pro Gly Glu Arg Gly Glu Pro Gly Ile Thr Gly Leu Pro Gly Glu
225                 230                 235                 240

Lys Gly Met Ala Gly Gly His Gly Pro Asp Gly Pro Lys Gly Ser Pro
                245                 250                 255

Gly Pro Ser Gly Thr Pro Gly Asp Thr Gly Pro Pro Gly Leu Gln Gly
                260                 265                 270

Met Pro Gly Glu Arg Gly Ile Ala Gly Thr Pro Gly Pro Lys Gly Asp
            275                 280                 285

Arg Gly Gly Ile Gly Glu Lys Gly Ala Glu Gly Thr Ala Gly Asn Asp
290                 295                 300

Gly Ala Gly Gly Leu Pro Gly Pro Leu Gly Pro Gly Pro Ala Gly
305                 310                 315                 320

Leu Leu Gly Glu Lys Gly Glu Pro Gly Arg Gly Leu Val Gly Pro
                325                 330                 335

Pro Gly Ser Arg Gly Asn Pro Gly Ser Arg Gly Glu Asn Gly Pro Thr
            340                 345                 350

Gly Ala Val Gly Phe Ala Gly Pro Gln Gly Ser Asp Gly Gln Pro Gly
            355                 360                 365

Val Lys Gly Glu Pro Gly Glu Pro Gly Gln Lys Gly Asp Ala Gly Ser
        370                 375                 380

Pro Gly Pro Gln Gly Leu Ala Gly Ser Pro Gly Pro His Gly Pro Asn
385                 390                 395                 400
```

```
Gly Val Pro Gly Leu Lys Gly Gly Arg Gly Thr Gln Gly Pro Pro Gly
                405             410                 415

Ala Thr Gly Phe Pro Gly Ser Ala Gly Arg Val Gly Pro Pro Gly Pro
                420             425                 430

Ala Gly Ala Pro Gly Pro Ala Gly Pro Leu Gly Glu Pro Gly Lys Glu
            435             440                 445

Gly Pro Pro Gly Pro Arg Gly Asp Pro Gly Ser His Gly Arg Val Gly
    450             455                 460

Val Arg Gly Pro Ala Gly Pro Pro Gly Gly Pro Gly Asp Lys Gly Asp
465             470                 475                     480

Pro Gly Glu Asp Gly Gln Pro Gly Pro Asp Gly Pro Gly Pro Gly Ala
            485                 490                 495

Gly Thr Thr Gly Gln Arg Gly Ile Val Gly Met Pro Gly Gln Arg Gly
            500                 505             510

Glu Arg Gly Met Pro Gly Leu Pro Gly Pro Ala Gly Thr Pro Gly Lys
            515             520                 525

Val Gly Pro Thr Gly Ala Thr Gly Asp Lys Gly Pro Pro Gly Pro Val
    530             535                 540

Gly Pro Pro Gly Ser Asn Gly Pro Val Gly Glu Pro Gly Pro Glu Gly
545             550             555                     560

Pro Ala Gly Asn Asp Gly Thr Pro Gly Arg Asp Gly Ala Val Gly Glu
            565                 570                 575

Arg Gly Asp Arg Gly Asp Pro Gly Pro Ala Gly Leu Pro Gly Ser Gln
            580                 585                 590

Gly Ala Pro Gly Thr Pro Gly Pro Val Gly Ala Pro Gly Asp Ala Gly
        595             600                 605

Gln Arg Gly Asp Pro Gly Ser Arg Gly Pro Ile Gly His Leu Gly Arg
        610                 615             620

Ala
625
```

METHOD FOR PREVENTION OF PLATELET AGGREGATION EMPLOYING AND RGD-ENRICHED GELATINE-LIKE PROTEIN

CROSS-REFERENCE TO RELATED APPLICATIONS

This application is a continuation of application Ser. No. 11/770,256 filed Jun. 28, 2007 (now U.S. Pat. No. 7,560,427), which is a divisional of application ser. No. 10/550,786 filed Sep. 27, 2005 (now U.S. Pat. No. 7,517,954, which is the National Stage Entry of PCT/NL04/00208 filed Mar. 26, 2004, which latter application claims priority from European Patent Application No. 03075906.2 filed 28 Mar. 2003. The entire disclosure of each one of the aforesaid applications is incorporated herein by reference thereto.

FIELD OF THE INVENTION

The invention relates to RGD-enriched gelatines that are used for attachment to integrins. The invention further relates to cell supports coated with RGD-enriched gelatines. Said cell supports may be of use in cell culture work and applications involving cell cultures of anchor dependent cells and also in a large variety of medical applications.

BACKGROUND OF THE INVENTION

Cell culture of animal cells, in particular mammalian cells, is important for the production of many important (genetically engineered) biological materials such as vaccines, enzymes, hormones and antibodies. The majority of animal cells are anchorage-dependent and require attachment to a surface for their survival and growth.

Routinely, anchorage-dependent cells have been cultivated on the walls of for instance tissue culture flasks and roller bottles. As the necessity has developed to provide large amounts of certain antiviral vaccines, genetically engineered proteins, and other cell-derived products, improvements have been made to develop new systems for larger scale production of cells.

One such an improvement started with the development of microcarriers in 1967 by Van Wezel (Van Wezel, A. L. *Nature* 216:64-65 (1967)). Van Wezel made micro-carriers composed of cross-linked dextran beads charged with tertiary amine groups (DEAE). He demonstrated the attachment and growth of cells on these positively charged DEAE-dextran beads suspended in culture media in a stirred vessel. Thus, in microcarrier cell cultures cells grow as monolayers on small spheres which are in suspension. By using microcarriers it is possible to achieve yields of several million cells per milliliter. Over the years various types of microcarriers have been developed. For instance glass beads and polystyrene beads have been described. Cross-linked dextran, like the first microcarriers, is still the most popular bead material.

Some advantages of microcarrier cultures over other methods of large-scale cultivation are: i) high surface area to volume ratio can be achieved which can be varied by changing the microcarrier concentration leading to high cell densities per unit volume with a potential for obtaining highly concentrated cell products; ii) cell propagation can be carried out in a single high productivity vessel instead of using many low productivity units, thus achieving a better utilisation and a considerable saving of medium; iii) since the microcarrier culture is well mixed, it is easy to monitor and control different environmental conditions such as pH, $pO_2$, $pCO_2$ etc.; iv) cell sampling is easy; v) since the beads settle down easily, cell harvesting and downstream processing of products is easy; vi) microcarrier cultures can be relatively easily scaled up using conventional equipment like fermenters that have been suitably modified.

When developing further improvements the following requirements for an optimum microcarrier should be met: i) the surface properties of the beads should be such that cells can adhere and proliferate rapidly, preferably the contour should be even; ii) the density of the beads should be slightly more than that of the culture medium, so as to facilitate easy separation; conventional culture media are aqueous in nature and have densities ranging from 1.03-1.09 g/cc, however, the density should not exceed a certain limit the optimum range being 1.03-1.045 g/ml; gentle stirring, which will not harm the shear-sensitive cells, should be sufficient to keep them in suspension, if the beads settle cell growth will be prevented; iii) the size-distribution of the beads should be narrow so that an even suspension of all microcarriers is achieved and cells attain confluency at approximately the same time; also, clustering of microcarriers in solution should be prevented; iv) the optical properties should enable easy microscopic observation; v) they should be non-toxic not only for the survival and good growth of the cells but also for cell culture products that are used for veterinary or clinical purposes; vi) the matrix of the beads should be such that collisions, which occur during stirring of the culture, do not cause fragmentation of the beads.

An important modification in the development of improved microcarriers is the coating of core particles with collagen. The advantage of using collagen is that it is a promoter for both cell attachment and cell growth. In addition cells can be easily detached by proteolytic enzymes. Also microcarriers coated with fibronectin, which is a cell adhesion promoter, have been described.

Cell surface receptors that are involved in binding are identified as integrins. More than 20 integrins are known, each having different ligand specificities. Many integrins can recognise the amino acid sequence RGD (arginine-glycine-aspartic acid). The number of proteins known to comprise an RGD sequence is limited, estimated to be approximately 400. Also not every occurring RGD sequence is involved in a binding function. In particular RGDS is known to be involved in cell adhesion. It is known that natural native collagens comprise the amino acid sequence RGD. Examples are for instance murine COL1A1-1, COL1A1-2, COL1A1-3, rat COL3A1, human COL1A-1, COL2A-1, COL3A-1 and COL1A1-2. Cell attachment to collagen follows a highly specific mechanism, as cells secrete the protein fibronectin which has a specific affinity for collagen. After attachment to collagen, the fibronectin binds subsequently to the integrin proteins in the cell.

Gelatine is a degradation product of collagen, and the term truly reflects a heterogeneous mixture of proteins and peptides with MW's ranging from 5,000 up to more than 400,000 daltons. A certain fraction of these gelatine polymers will contain an RGD motive and a certain fraction of hydrolysed molecules will not have such an RGD motif.

Burgess and Myles describe the chemical coupling of RGD containing peptides to type I collagen, which method is complicated and introduces impurities into the target materials and has limited modification freedom (Ann Biomed Eng 2000 January; 28(1): 110-118).

U.S. Pat. No. 5,512,474 aims at a good cell adhesion by combining cell adhesion factors and positively charged molecules to the surface of a cell culture support. Fibronectin is identified as a cell adhesion intermediate.

U.S. Pat. No. 5,514,581 is concerned with the production of substantially new polypeptides by using automated methods for the chemical synthesis of DNA in combination with recombinant DNA technology. The patent describes non-natural polypeptides which may be of use in commercial applications for which known, naturally occurring polypeptides are not appropriate. Although the artificial proteins could contain an RGD sequence, the resulting bio-polymers have little resemblance with naturally occurring proteins, and will cause immunological problems in case of medical applications.

Cell attachment also plays an important role in medical applications such as wound treatment (including artificial skin materials), bone and cartilage (re)growth and implantations and artificial blood vessel materials. Thus in medical applications often the demand is that a material has a biocompatible coating in terms of cell attachment. In general collagen is preferred over structures like those described in U.S. Pat. No. 5,514,581 since collagen has a low antigenicity and is present in both skin and bone or cartilage. Microcarriers coated with gelatine are applied, but also porous matrixes of collagen are used. An example is collagen coated beads to grow keratinocytes and the subsequent transplantation of the beads containing keratinocytes to promote healing of wounds is described in U.S. Pat. No. 5,972,332. Another area of interest in relation to cell attachment is the blocking of attachment receptors of cells. For instance by blocking the attachment receptors cancer metastasis may be influenced or inhibited. Also smaller peptides with RGD sequences are used to block the binding sites on cells thus preventing unwanted interactions like aggregation or coagulation as described for example in EP 628,571.

There is however an urgently felt need for further improvements of materials for use in applications involving cell attachment. The fibronectin-mediated cell attachment mechanism is effectuated to attach cells to natural gelatines. However, natural gelatines are not safe in terms of prion and virus impurities. The RGD mediated mechanism for cell attachment is effectuated by several artificial bio-polymers, produced by chemical or by recombinant DNA technologies. However, these materials have non-natural sequences and have a risk of initiating an immunological response which could result in serious medical problems.

Whereas often the terms 'collagen', 'collagen-related', collagen-derived' or the like are also used in the art, the term 'gelatine' or 'gelatine-like' protein will be used throughout the rest of this description. Natural gelatine is a mixture of individual polymers with MW's ranging from 5,000 up to more than 400,000 daltons. The terms cell adhesion and cell attachment are used interchangeably. Also the terms RGD sequence and RGD motif are used interchangeably.

SUMMARY OF THE INVENTION

It is an object of the invention to provide polypeptides or peptides which have an improved, preferably a high cell binding capacity and selectivity. A further object of the invention is to provide cell binding peptides or polypeptides with no risk for viral infection or other pathogens or health related hazards such as prions. It is also an object of the invention to provide peptides or polypeptides which do not evoke any immune response when being in contact, directly or indirectly, with the human immune system.

Surprisingly it was found that all these objectives were met by an RGD-enriched gelatine with a more even distribution of RGD sequences than occurring in a natural gelatine and with a minimum level of RGD sequences. The level of RGD sequences is expressed as a percentage. This percentage is calculated by dividing the number of RGD motifs divided by the total number of amino acids and multiplying the result with 100. Note that the highest percentage of RGD motifs, i.e. in a gelatine consisting solely of RGD motifs, would be 33.33. Also, the number of RGD motifs is an integer starting from 1, 2, 3, . . . etc.

The RGD-enriched gelatine of the invention is highly suitable for coating a cell culture support for growing anchor-dependant cell types. Thus the invention relates to a cell support comprising an RGD-enriched gelatine in which the percentage of RGD motifs related to the total number of amino acids is at least 0.4 and if the RGD-enriched gelatine comprises 350 amino acids or more, each stretch of 350 amino acids contains at least one RGD motif.

The invention provides RGD-enriched gelatine for binding to integrins in which the percentage of RGD motifs related to the total number of amino acids is at least 0.4 and if the RGD-enriched gelatine comprises 350 amino acids or more, each stretch of 350 amino acids contains at least one RGD motif and said gelatine consists for at least 80% of one or more parts of native human collagen sequences and said parts of native human collagen sequences have a length of at least 30 amino acids.

Also the invention relates to the use of an RGD-enriched gelatine according to the invention as a coating on scaffolds for tissue engineering or on implant or transplant materials.

Further the RGD-enriched gelatine of the invention is designed for use in medical applications, in particular as a coating on implant or transplant material or as a component of drug delivery systems, for inhibition of cancer metastasis, for prevention of platelet aggregation, for use as an antithrombic agent, for use as tissue adhesive, for dental products, for use as artificial skin matrix material and for use after surgery to prevent tissue adhesion.

DESCRIPTION OF THE INVENTION

The present invention is directed to peptides polypeptides or proteins, in particular to gelatines or gelatine-like proteins, which are highly suitable for cell adhesion and can be used in medical or biotechnological applications. More specifically the invention is directed to cell binding peptides or polypeptides that have a low antigenicity and that can be used without the risk of transferring pathological factors such as viruses, prions and the like.

It was found, surprisingly, that it is possible to obtain peptides or polypeptides with excellent cell attachment properties and which do not display any health related risks by production of RGD-enriched gelatines in which the percentage of RGD motifs related to the total number of amino acids is at least 0.4. If the RGD-enriched gelatine comprises 350 amino acids or more, each stretch of 350 amino acids contains at least one RGD motif. Preferably the percentage of RGD motifs is at least 0.6, more preferably at least 0.8, more preferably at least 1.0, more preferably at least 1.2 and most preferably at least 1.5. Such (recombinant) gelatines are very suitable for coating cell culture supports which can be used in biotechnological processes or in medical applications. In the context of this invention a "cell support" is a substance that gives support to cells to facilitate their growth and multiplication.

A percentage RGD motifs of 0.4 corresponds with at least 1 RGD sequence per 250 amino acids. The number of RGD motifs is an integer, thus to meet the feature of 0.4%, a gelatine consisting of 251 amino acids should comprise at least 2 RGD sequences. Preferably the RGD-enriched recombinant gelatine of the invention comprises at least 2 RGD sequence per 250 amino acids, more preferably at least 3 RGD sequences per 250 amino acids, most preferably at least 4 RGD sequences per 250 amino acids. In a further embodiment an RGD-enriched gelatine according to the invention comprises at least 4 RGD motifs, preferably 6, more preferably 8, even more preferably 12 up to and including 16 RGD motifs.

The term 'RGD-enriched gelatine' in the context of this invention means that the gelatines of this invention have a certain level of RGD motifs, calculated as a percentage of the total number of amino acids per molecule and a more even distribution of RGD sequences in the amino acid chain than a natural gelatine. In humans up to date 26 distinct collagen types have been found on the basis of protein and or DNA sequence information (see K. Gelse et al, Collagens-structure, function and biosynthesis, Advanced Drug Delivery reviews 55 (2003) 1531-1546). Sequences of natural gelatines, both of human and non-human origin, are described in the Swiss-Prot protein database. Herebelow follows a list of suitable human native sequences, identified by their entry name and primary accession number in the Swiss-Prot database, that may serve as a source of parts of natural sequences comprised in the RGD-enriched gelatines of this invention.

CA11_HUMAN (P02452) Collagen alpha 1(I) chain precursor. {GENE: COL1A1}—*Homo sapiens* (Human)
CA12_HUMAN (P02458) Collagen alpha 1(II) chain precursor [Contains: Chondrocalcin]. {GENE: COL2A1}—*Homo sapiens* (Human)
CA13_HUMAN (P02461) Collagen alpha 1(111) chain precursor. {GENE: COL3A1}—*Homo sapiens* (Human)
CA14_HUMAN (P02462) Collagen alpha 1(IV) chain precursor. {GENE: COL4A1}—*Homo sapiens* (Human)
CA15_HUMAN (P20908) Collagen alpha 1(V) chain precursor. {GENE: COL5A1}—*Homo sapiens* (Human)
CA16_HUMAN (P12109) Collagen alpha 1(VI) chain precursor. {GENE: COL6A1}—*Homo sapiens* (Human)
CA17_HUMAN (Q02388) Collagen alpha 1(VII) chain precursor (Long-chain collagen) (LC collagen). {GENE: COL7A1}—*Homo sapiens* (Human)
CA18_HUMAN (P27658) Collagen alpha 1(VIII) chain precursor (Endothelial collagen). {GENE: COL8A1}—*Homo sapiens* (Human)
CA19_HUMAN (P20849) Collagen alpha 1(IX) chain precursor. {GENE: COL9A1}—*Homo sapiens* (Human)
CA1A_HUMAN (Q03692) Collagen alpha 1(X) chain precursor. {GENE: COL10A1}—*Homo sapiens* (Human)
CA1B_HUMAN (P12107) Collagen alpha 1(XI) chain precursor. {GENE: COL11A1}—*Homo sapiens* (Human)
CA1C_HUMAN (Q99715) Collagen alpha 1(XII) chain precursor. {GENE: COL12A1}—*Homo sapiens* (Human)
CA1E_HUMAN (P39059) Collagen alpha 1(XV) chain precursor. {GENE: COL15A1}—*Homo sapiens* (Human)
CA1F_HUMAN (Q07092) Collagen alpha 1(XVI) chain precursor. {GENE: COL16A1}—*Homo sapiens* (Human)
CA1G_HUMAN (Q9UMD9) Collagen alpha 1(XVII) chain (Bullous pemphigoid antigen 2) (180 kDa bullous pemphigoid antigen 2). {GENE: COL17A1 OR BPAG2 OR BP180}—*Homo sapiens* (Human)
CA1H_HUMAN (P39060) Collagen alpha 1(XVIII) chain precursor [Contains: Endostatin]. {GENE: COL18A1}—*Homo sapiens* (Human)
CA1I_HUMAN (Q14993) Collagen alpha 1(XIX) chain precursor (Collagen alpha 1(Y) chain). {GENE: COL19A1}—*Homo sapiens* (Human)
CA21_HUMAN (P08123) Collagen alpha 2(I) chain precursor. {GENE: COL1A2}—*Homo sapiens* (Human)
CA24_HUMAN (P08572) Collagen alpha 2(IV) chain precursor. {GENE: COL4A2}—*Homo sapiens* (Human)
CA25_HUMAN (P05997) Collagen alpha 2(V) chain precursor. {GENE: COL5A2}—*Homo sapiens* (Human)
CA26_HUMAN (P12110) Collagen alpha 2(VI) chain precursor. {GENE: COL6A2}—*Homo sapiens* (Human)
CA28_HUMAN (P25067) Collagen alpha 2(VIII) chain precursor (Endothelial collagen). {GENE: COL8A2}—*Homo sapiens* (Human)
CA29_HUMAN (Q14055) Collagen alpha 2(IX) chain precursor. {GENE: COL9A2}—*Homo sapiens* (Human)
CA2B_HUMAN (P13942) Collagen alpha 2(XI) chain precursor. {GENE: COL11A2}—*Homo sapiens* (Human)
CA34_HUMAN (Q01955) Collagen alpha 3(IV) chain precursor (Goodpasture antigen). {GENE: COL4A3}—*Homo sapiens* (Human)
CA35_HUMAN (P25940) Collagen alpha 3(V) chain precursor. {GENE: COL5A3}—*Homo sapiens* (Human)
CA36_HUMAN (P12111) Collagen alpha 3(VI) chain precursor. {GENE: COL6A3}—*Homo sapiens* (Human)
CA39_HUMAN (Q14050) Collagen alpha 3(IX) chain precursor. {GENE: COL9A3}—*Homo sapiens* (Human)
CA44_HUMAN (P53420) Collagen alpha 4(IV) chain precursor. {GENE: COL4A4}—*Homo sapiens* (Human)
CA54_HUMAN (P29400) Collagen alpha 5(IV) chain precursor. {GENE: COL4A5}—*Homo sapiens* (Human)
CA64_HUMAN (Q14031) Collagen alpha 6(IV) chain precursor. {GENE: COL4A6}—*Homo sapiens* (Human)
EMD2_HUMAN (Q96A83) Collagen alpha 1 (XXVI) chain precursor (EMI domain containing protein 2) (Emu2 protein) (Emilin and multimerin-domain containing protein 2). {GENE: EMID2OR COL26A1 OR EMU2}—*Homo sapiens* (Human)

Natural gelatines are known to comprise RGD sequences. It is important however that a gelatine molecule does not contain too large parts without RGD motifs. Too large parts of gelatines without RGD sequence reduce the possibility of cell attachment when such a gelatine is used for instance as a coating on a microcarrier. Apparently not all RGD sequences in a gelatine are under all circumstances available for cell attachment. It was found that cell attachment was remarkably improved in gelatines according to the invention compared to gelatines having a stretch of amino acids of more than 350 without an RGD sequence. For gelatines of less than 350 amino acids it is sufficient to have a percentage of RGD sequences of at least 0.4. Note that for a gelatine of 251-350 amino acids this means that at least 2 RGD motifs are present.

In a preferred embodiment the RGD-enriched gelatine is prepared by recombinant DNA technology. Recombinant gelatines of this invention are preferably derived from collageneous sequences. Nucleic acid sequences encoding collagens have been generally described in the art. (See, e.g., Fuller and Boedtker (1981) Biochemistry 20: 996-1006; Sandell et al. (1984) J Biol Chem 259: 7826-34; Kohno et al. (1984) J Biol Chem 259: 13668-13673; French et al. (1985) Gene 39: 31-312; Metsaranta et al. (1991) J Biol Chem 266: 16862-16869; Metsaranta et al. (1991) Biochim Biophys Acta 1089: 241-243; Wood et al. (1987) Gene 61: 225-230; Glumoff et al. (1994) Biochim Biophys Acta 1217: 41-48; Shirai et al. (1998) Matrix Biology 17: 85-88; Tromp et al. (1988) Biochem J 253: 919-912; Kuivaniemi et al. (1988) Biochem J 252: 633640; and Ala-Kokko et al. (1989) Biochem J 260: 509-516.).

For pharmaceutical and medical uses, recombinant gelatines with amino acid sequences closely related to or identical to amino acid sequences of natural human collagens are preferred. More preferably the amino acid sequence of the inventive gelatine is designed by a repetitive use of a selected amino acid sequence of a human collagen. A part of a natural collagen sequence comprising an RGD motif is selected. The percentage of RGD motifs in such a selected sequence depends on the chosen length of the selected sequence, selection of a shorter sequence results in a higher RGD percentage. Repetitive use of a selected amino acid sequence results in a gelatine with a higher molecular weight, which is non-antigenic and with an increased number of RGD motifs (compared to natural gelatines or collagens). Natural non-human sources include non-human mammalian sources, such as bovine, porcine, and equine sources, and other animal sources, such as chicken, murine, rat and piscine sources.

Thus in a preferred embodiment the RGD-enriched gelatine according to the invention comprises a part of a native human collagen sequence. Preferably the RGD-enriched gelatine consists for at least 80% of one or more parts of one or more native human collagen sequences. Each of such parts of human collagen sequences should have a length of at least 30 amino acids, more preferably at least 45 amino acids, most preferably at least 60 amino acids, up to e.g. 240, preferably up to 150, most preferably up to 120 amino acids, each part preferably containing one or more RGD sequences. Preferably the RGD-enriched gelatine consists of one or more parts of one or more native human collagen sequences.

An example of a suitable source of a gelatine according to this invention is human COL1A1-1. A part of 250 amino acids comprising an RGD sequence is given in SEQ ID NO: 1.

RGD sequences in gelatines can adhere to specific receptors on the cell wall called integrins. These integrins differ in their specificity in recognising cell binding amino acid sequences. Although both natural gelatine and, for example, fibronectin may contain RGD sequences, gelatine can bind cells that will not bind to fibronectin and vice versa. Therefore fibronectin comprising RGD sequences cannot always replace gelatine for cell adhesion purposes.

Recombinantly produced gelatine does not suffer from the disadvantage of contamination with pathogens originating from the animal from which the gelatine was derived.

When used as or in combination with a cell culture support, gelatine functions as a cell binding polypeptide. It has the advantage over other polypeptides that it can also be metabolised by the cells growing on it. A further advantage is that it can be easily digested enzymatically so that cells can be harvested with almost 100% yield. A further advantage of recombinantly produced gelatines is that the molecular weight (MW) can be kept uniform. Natural gelatines unavoidably have a broad molecular weight distribution with peptides smaller than 5,000 kD up to large polymers with a molecular weight larger than 400,000 kD, resulting from the production method. In particular in combination with microcarrier core beads as cell culture support, a disadvantage of smaller peptides is that they will adhere inside finer pores of the microcarrier which cannot be reached by the cells so that part of the added gelatine is not used. With recombinant production methods the gelatine can be designed with the desired molecular weight, preventing this undesired loss of material.

In a further embodiment the gelatine of the invention has a molecular weight of about 30 kDa to about 200 kDa to coat a core bead resulting in a cell culture support in the form of a microcarrier.

In addition to the presence of RGD sequences, the molecular weight range of the gelatine offers striking advantages and provides the resulting microcarriers with advantageous properties. A key problem in the process of coating microcarrier core beads is the clumping together of beads. In particular such clumping reduces the available surface area for cell attachment and disturbs the size distribution of the microcarriers rendering them unusable.

It was found that the relatively small fraction of high MW gelatine polymer molecules within a natural gelatine batch is to a large extent responsible for the clumping together of beads during the microcarrier production process. It was concluded that when such a gelatine polymer with high molecular weight adheres to a core bead, a part of the peptide chain may point away from the surface of the core bead and as such be an anchor for other beads and thus induce coagulation.

It is therefore preferred according to the present invention to coat core beads with gelatine having a molecular weight of less than 200 kDa, more preferably less than 150 kDa.

Furthermore, it was found that the small MW fraction of a natural gelatine shows unfavourable microcarrier coating characteristics. This small MW fraction showed a lower adsorption force to the microcarrier beads, and, thus, when not being adsorbed it promotes microcarrier clumping after the chemical cross-linking step. Additionally, in case of the use of lower concentrations of the gelatine in the microcarrier coating process to prevent clumping, the small MW fraction is at first instance adsorbed to the microcarrier but has the unfavourable characteristic of entering the small pores of a microcarrier porous core beads, thereby not contributing to the attachment of the cells on the microcarrier during the cell culture step. Thus, the molecular weight of the gelatine should be high enough to perform the actual coating process effectively resulting in efficient coating, to prevent clumping of the core beads and to prevent loss of the gelatine. Thus the molecular weight of the gelatine should be higher than 30 kDa, preferably higher than 60 kDa, most preferably higher than 70 kDa.

Preferably the molecular weight of the gelatine or gelatine-like protein is uniform, with more than 75%, preferably more than 85%, more preferably more than 95% or even at least 98% of the gelatine or gelatine-like protein having a uniform MW within 20% from the selected molecular weight.

By selecting a molecular weight, within the above specified range, in a coating process the viscosity of the gelatine or gelatine-like protein coating solution can be accurately controlled. Complete or, more important, partial gelling of such a gelatine solution can be prevented while being able to select a high as possible concentration of the gelatine. The uniform gelatine ensures a process of identically coated microcarriers. The uniform coating process allows the use of a minimum amount of gelatine and the use of a minimum volume of gelatine coating solution. All this results in a far more efficient coating process than that is known in the art.

In one embodiment of the invention non-porous core beads are coated with gelatine of the invention. Suitably non-porous core beads are made of polystyrene or glass. Other suitable non-porous materials are known to those skilled in the art.

A particular advantageous embodiment is the process of the invention wherein porous core beads, such as beads from modified dextran or cross-linked cellulose, or (porous) polystyrene, in particular DEAE-dextran, are coated with gelatine of the invention. Other suitable porous materials are known to those skilled in the art, and include e.g. other chemically modified or non-modified polysaccharides. The lower molecular weight limit prevents that gelatine or gelatine-like protein enters the pores of the porous core beads thereby preventing inefficient coating of the beads and unnecessary loss of gelatine or gelatine-like protein.

The size of the beads may vary from 50 μm to 500 μm. Typical mean microcarrier bead sizes are about 100, about 150 or about 200 µm in physiological saline. Size ranges with at least 90% of the beads lying within the range may vary from 80-120 µm, 100-150 µm, 125-175 µm or 150-200 µm.

A wide range of cells may be cultured on microcarriers. For instance, cells from invertebrates, from fish, birds and cells of mammalian origin may be cultivated on microcarriers. Transformed and normal cell lines, fibroblastic and epithelial cells and even genetically engineered cells may be cultivated on microcarriers for various biological applications such as for the production of immunologicals like interferons, interleukins, growth factors etc. Cells cultured on microcarriers also serve as hosts for a variety of viruses that are used as vaccines like foot and mouth disease or rabies.

Microcarrier cultures have a wide number of applications other than mass cultivation as well. Cells growing on microcarriers serve as an excellent tool for studying different aspects of cell biology such as cell-to-cell or cell-to-substratum interactions. Cell differentiation and maturation, metabolic studies may also be carried out using microcarriers. Such cells can also be used for electron microscopic studies or for the isolation of cell organelles such as the cell membrane. Also, this system is essentially a three-dimensional system and serves as a good 3-D model. Similarly, co-cultivation of cells can be done using this system. Thus applications include the production of large quantities of cells, viruses and cell products (e.g. interferon, enzymes, nucleic acids, hormones), studies on cell adhesion, differentiation and cell function, perfusion column culture systems, microscopy studies, harvesting mitotic cells, isolation of cells, membrane studies, storage and transport of cells, assays involving cell transfer and studies on uptake of labelled compounds.

Microcarriers may also be used for the depletion of macrophages from a population of spleen cells. DEAE-dextran microcarriers can potentiate stimulation of lymphocytes by concanavalin A (con A). Microcarrier beads confluent with allogenic tumour cells can be injected in mice to increase humoral and cell-mediated immunity. Plant protoplasts can be immobilised on DEAE-dextran microcarriers.

As a result of the large surface area to volume ratio provided by microcarriers, they can successfully be used for a variety of biological productions on a laboratory scale as well as an industrial scale of for instance even 4000 liters or more.

Large scale production of expressed products can be accomplished with gelatine-coated microcarriers. Loading of microcarriers in production scale bioreactors is generally 20 g/l, but may be increased up to 40 g/l. Microcarriers may be used in batch and perfusion systems, in stirred cultures, and wave bioreactors, as well as to increase the surface area of traditional stationary monolayers and roller cultures.

In a further preferred embodiment the gelatine or gelatine-like protein is in essence free of hydroxyproline residues. Hydroxylation is a requirement for the formation of triple helices in collagen and plays a role in gelation of gelatine. In particular less than 10%, more preferably less than 5% of the amino acid residues of the recombinant gelatines are hydroxyprolines, preferably the recombinant gelatine is free from hydroxyprolines in applications where the gelling capability of the recombinant gelatine is unfavourable. The hydroxyproline-free recombinant gelatines can be used in higher concentrations, and the solutions will be less viscous requiring less vigorous agitation, resulting in less shear forces on the cultured cells. As described in WO 02/070000 A1, recombinant gelatines which are is essence free from hydroxyprolines do not show immune reactions involving IgE in contrast to natural gelatine.

A process for the preparation of collagen coated microcarriers is described in U.S. Pat. No. 4,994,388. In short providing a core bead with a collagen coating is performed in two steps: coating and fixing. The core beads are suspended in an acidic, aqueous collagen solution (0.01-0.1N acetic acid), and the solution is evaporated to dryness. The dry, collagen-coated beads are then suspended in a solution which contains a protein cross-linking agent such as glutaraldehyde, thus cross-linking the collagen coating. Alternatively, the core beads wetted with the collagen solution are not dried entirely before the start of the fixing step. Variations in coating conditions and alternative coating processes are well within the competence of those skilled in the art.

Recombinant structures can also be designed to incorporate additional positively charged groups, as in U.S. Pat. No. 5,512,474, by building in additional arginines, lysines or histidines. Recombinant production of gelatines allows easy manipulation of the number of positively charged amino acids, meaning positively charged at the pH of the cell culture, in the produced protein. In particular arginine, lysine and histidine carry positive charges. It is well within the reach of the skilled person to design a gelatine with a net positive charge at the pH of the particular cell culture of interest. Cells are normally cultured at a pH of 7-7.5. Thus in a further embodiment of the invention a gelatine or gelatine-like protein is used that has a net positive charge at pH 7-7.5. Preferably the net positive charge is +2, +3, +4, +5, +10 or higher. Thus in a further embodiment the invention relates to a gelatine that has a net positive charge at pH 7-7.5. Preferably the net positive charge is +2, +3, +4, +5, +10 or higher In a further embodiment the invention relates to RGD-enriched gelatines of at most 10 kDa, preferably at most 5 kDa. Such an RGD-enriched gelatine containing at least one RGD sequence can be used to block surface receptors on cells. Blocking of receptors of cells is applied in for example inhibiting angiogenesis or in blocking integrins on cardiac fibroblasts.

Cell supports coated with recombinant gelatine according to the invention, on which cells have been grown can be applied during, for example, transplantation of skin or wound treatment or to enhance bone or cartilage (re)growth. It is also possible to coat implant materials with recombinant gelatine of the invention to adhere cells which promote implantation.

Thus a specific embodiment is a cell support according to this invention, said cell support being a microcarrier Other particular embodiments are cell supports selected from the group consisting of an RGD-enriched coated implant or transplant material, an RGD-enriched coated scaffold for tissue engineering, (part of) a dental product, (part of) a wound healing product, (part of) artificial skin matrix material and (part of) a tissue adhesive.

A natural gelatine molecule in its primary amino acid sequence basically consists of repeats of GXY triplets, thus approximately one third of the total number of amino acids is a glycine. The molecular weight of gelatine is typically large, values of the molecular weight vary from 10,000 to 300,000 Dalton and higher.

In a further embodiment the invention relates to RGD-enriched gelatines which are not glycosylated. Glycosylation takes place at the amino acids Asn (N-glycosydic structures), or Ser or Thr (O-glycosydic structures). Glycosylation should be preferably prevented for applications where no immune response is desired. The absence of Asn, Ser and Thr amino acids in the primary sequence is an effective way to prevent the glycosylation in biotechnological production systems using for instance yeast cell cultures.

Furthermore, characteristic for gelatine is the unusual high content of proline residues. Even more characteristic is that in natural gelatine a number of the proline residues is hydroxylated. Most prominent site of hydroxylation is the 4-position resulting in the presence in the gelatine molecule of the unusual amino acid 4-hydroxyproline. In a triplet 4-hydroxyproline is always found in the Y position. The presence of the hydroxyproline residues is responsible for the fact that a gelatine molecule in its secondary structure can adopt a helical conformation. Thus, it is preferred that the gelatines to be used according to the invention in applications in which the gelling property is unfavourable contain less than 5%, preferably less than 3%, most preferably less than 1% of hydroxyproline residues.

In this invention gelatine-like proteins are to be understood as proteins in which GXY triplets or stretches of GXY triplets are separated by one or more amino acids.

The RGD-enriched gelatines according to the invention can be produced by recombinant methods as disclosed in EP-A-0926543, EP-A-1014176 or WO01/34646. Also for enablement of the production and purification of gelatines of the invention reference is made to the examples in EP-A-0926543 and EP-A-1014176.

The preferred method for producing an RGD-enriched gelatine is by starting with a natural nucleic acid sequence encoding a part of the collagen protein that includes an RGD amino acid sequence. By repeating this sequence an RGD-enriched gelatine is obtained.

If X-RGD-Y is a part of the natural collagen amino acid sequence, a (part of a) gelatine with three RGD amino acid sequences would have the structure -X-RGD-Y-$(GXY)_n$-GX-RGD-Y-$(GXY)_n$-GX-RGD-Y-, with n being an integer starting from 0. By varying n the number of RGD sequences on the total amino acids number can be controlled. A clear advantage of this method is that the amino acid sequence remains most natural and thus has the lowest risk of inducing immunological response in clinical applications.

Starting from a natural nucleic acid sequence encoding (part of) a collagen, also point mutations can be applied so as to yield a sequence encoding an RGD sequence. Based on the known codons a point mutation can be performed so that an RGX sequence after mutation will yield an RGD sequence, alternatively also an YGD sequence can be mutated to yield an RGD sequence. Also it is possible to carry out two mutations so that an YGX sequence will give an RGD sequence. Also it may be possible to insert one or more nucleotides or delete one or more nucleotides giving rise to a desired RGD sequence.

Thus the gelatine-like proteins can be produced by expression of nucleic acid sequence encoding such polypeptide by a suitable micro-organism. The process can suitably be carried out with a fungal cell or a yeast cell. Suitably the host cell is a high expression host cells like *Hansenula, Trichoderma, Aspergillus, Penicillium, Saccharomyces, Kluyveromyces, Neurospora* or *Pichia*. Fungal and yeast cells are preferred to bacteria as they are less susceptible to improper expression of repetitive sequences. Most preferably the host will not have a high level of proteases that attack the collagen structure expressed. In this respect *Pichia* or *Hansenula* offers an example of a very suitable expression system. Use of *Pichia pastoris* as an expression system is disclosed in EP-A-0926543 and EP-A-1014176. In one embodiment the microorganism is free of active post-translational processing mechanism such as in particular hydroxylation of proline and also hydroxylation of lysine. In another embodiment the host system has an endogenic proline hydroxylation activity by which the recombinant gelatine is hydroxylated in a highly effective way. The selection of a suitable host cell from known industrial enzyme producing fungal host cells specifically yeast cells on the basis of the required parameters described herein rendering the host cell suitable for expression of recombinant gelatine-like proteins suitable in compositions according to the invention in combination with knowledge regarding the host cells and the sequence to be expressed will be possible by a person skilled in the art.

EXAMPLES

Example 1

An RGD-enriched gelatine was produced by starting with the nucleic acid sequence that encodes for a part of the gelatine amino acid sequence of human COL1A1-1. The methods as disclosed in EP-A-0926543, EP-A-1014176 and WO01/34646 were used. The sequence of this RGD-enriched gelatine according to the invention is given in SEQ ID NO: 2. A total of four RGD sequences are present in the molecule which corresponds to a level of four RGD sequences per 250 amino acids. In a similar way gelatines with one and two RGD sequences per 250 amino acids were made.

Example 2

Preparation of Microcarriers Beads

Polystyrene beads with an average diameter of 100 micrometers are used. The heterobifunctional cross-linking agent, BBA-EAC-NOS, is used to covalently immobilise gelatine onto polystyrene beads. The BBA-EAC-NOS is added to the polystyrene beads and allowed to adsorb. Next, gelatine is added and is allowed to react with the NOS synthetic polymer to produce covalent coupling to the spacer. Then the beads are photoactivated (at 320 nm) to covalently immobilise the spacer (and covalently coupled gelatine) to the polystyrene beads. Finally, loosely adherent gelatine is removed by overnight washing with the mild detergent Tween 20 in phosphate buffered saline (pH 7.2).

Cell Types and Culture Conditions

Green monkey kidney (Vero) cells, Chinese hamster ovary (CHO) cells, normal rat kidney fibroblast (NRK-49F) cells, and Madin Darby canine kidney (MDCK) cells were purchased from ATCC. All four cell types were passaged and maintained in 75 cm@2 flasks at 37 DEG C. in a 5% CO2 environment. Vero and NRK-49F cells were cultured in Dulbecco's Modified Eagles's Medium (DMEM), CHO cells were cultured in Ham's F-12 Nutrient Mixture, and MDCK cells were cultured in Minimum Essential Medium (MEM) with Earle's salts.

With the Vero and CHO cells, the medium was supplemented with 10% fetal bovine serum (FBS), 2 mM L-glutamine, 20 mM HEPES buffer, 1 mM sodium pyruvate, 100 ug/ml streptomycin, and 100 units/ml penicillin (final pH 7.1). With the NRK-49F cells, the DMEM was supplemented with 5% FBS, 2 mM L-glutamine, 1 mM sodium pyruvate, non-essential amino acids (0.1 mM each), 100 ug/ml streptomycin, 100 units/ml penicillin, and 0.25 ug/ml of amphotericin B (final pH 7.1). With the MDCK cells, the MEM was supplemented with 10% FBS, 2 mM L-glutamine, non-essential amino acids (0.1 mM each), and 100 ug/ml streptomycin, 100 units/ml penicillin, and 0.25 ug/ml of amphotericin B (final pH 7.1).

In order to standardise the physiology of cells prior to each experiment, cells were passed into 150 cm@2 flasks 2 to 3 days prior to inoculation of microcarrier beads. Cells were trypsinised (0.05% trypsin, 0.53 mM EDTA in PBS) for removal from the flasks. For the microcarrier experiments, the cells were centrifuged to remove the trypsin medium and resuspended to about 1.times.10@6 cells/ml in culture medium. The viable cell concentration was determined by Trypan dye exclusion (0.4% Trypan blue in 0.9% saline).

Cell Culture and Assays in Spinner Flasks

For the cell attachment assay, 20 mg/ml of coated polystyrene beads were used and the cell concentration was 1.5.times.10@5 cells/ml for each cell type.

Microcarriers were cultured with 100 ml cultures being maintained in 250 ml spinner vessels and stirred with suspended magnetic impellers (50 rpm).

The kinetics of cell attachment were assayed as a decrease in supernatant cell concentration. For sample removal the agitation was stopped briefly (about 30 seconds) at which time the microcarriers settled and a supernatant sample was removed for cell quantitation as described below.

For the cell counts, the cells were stained by mixing with an equal volume of crystal violet (0.1% w/w) in 0.1 M citric acid, and then counted with a hemocytometer. Cell depletion from the medium was used as an indicator of cells attached to beads To verify that cells removed from the medium were indeed attached to microcarriers (and not lysed), cells attached to microcarriers were quantitated at the end of each cell attachment assay. One ml aliquots of well-agitated carrier medium were removed, the microcarriers were allowed to settle, and the settled microcarriers were resuspended in crystal violet/citric acid as described above. After incubating 1 hour at 37 DEG C., the suspension was sheared by sucking into and out of a Pasteur pipet to release nuclei, which were quantitated with a hemocytometer.

Gelatines with different RGD content were used as a microcarrier coating according to the foregoing procedure. Recombinant gelatines with no, one, two and four RGD sequences per 250 amino acids were tested. A clear correlation was found between the number of RGD sites and the cell attachment. Best results were obtained at a level of four RGD sites per 250 amino acids.

Example 3

An RGD-enriched gelatine was produced by starting with the nucleic acid sequence that encodes for a part of the gelatine sequence of human COL5A2. The methods as disclosed in EP-A-0926543, EP-A-1014176 and WO01/34646 were used. The sequence of this RGD-enriched gelatine according to the invention is given in SEQ ID NO: 3. The percentage of RGD motifs in this sequence is 0.8 and a stretch of 435 amino acids without an RGD sequence is present.

The above mentioned gelatine was used as a microcarrier coating according to the procedure in example 2. The cell attachment of this gelatine was compared with a gelatine with two RGD motifs per 250 amino acids as mentioned in example 1. Although the percentage of RGD motifs in both gelatines is the same (0.8%) the gelatine from example 1 clearly gave a much better cell attachment. This is attributed to the more even distribution of RGD motifs.

The invention claimed is:

1. A method for prevention of platelet aggregation in a subject in need thereof, said method comprising administering to said subject an RGD-enriched gelatine comprising at least 4 RGD motifs, and having a percentage of RGD motifs relative to the total number of amino acids in the RGD-enriched gelatine of at least 1.5 wherein, if the RGD-enriched gelatine comprises 350 amino acids or more, each stretch of 350 amino acids contains at least one RGD motif.

2. The method according to claim 1, wherein the RGD-enriched gelatine comprises a proportion of RGD motifs of at least 4 per 250 amino acids.

3. The method according to claim 1, wherein the RGD-enriched gelatine comprises a number of RGD motifs selected from the group consisting of 6, 8, 12, and up to and including 16.

4. The method according to claim 1, wherein the RGD-enriched gelatine has a molecular weight in the range of from about 30 kDa to about 200 kDa.

5. The method according to claim 1, wherein the RGD-enriched gelatine has a molecular weight of at most 10 kDa.

6. The method according to claim 5, wherein the RGD-enriched gelatine has a molecular weight of at most 5 kDa.

7. The method according to claim 1, wherein the RGD-enriched gelatine comprises less than 5 percent hydroxyproline residues.

8. The method according to claim 1, wherein the RGD-enriched gelatine comprises less than 3 percent hydroxyproline residues.

9. The method according to claim 1, wherein the RGD-enriched gelatine has a net positive charge at a pH in the range of from pH 7 to pH 7.5.

* * * * *